Jan. 15, 1935. D. S. BYERS Plant Pat. 120

PEACH TREE

Filed Aug. 13, 1934

Inventor

Donald S. Byers

By Owen & Owen

Attorneys

Patented Jan. 15, 1935

Plant Pat. 120

UNITED STATES PATENT OFFICE

120

PEACH TREE

Donald S. Byers, Clyde, Ohio

Application August 13, 1934, Serial No. 739,582

1 Claim. (Cl. 47—62)

In the year 1925 I discovered a seedling peach tree having characteristics in all respects similar to those described below in connection with certain of its reproductions. The parentage of the seedling is not certain, but the seed is believed to have been from an Elberta peach tree. I reproduced this tree by budding, and it was not asexually reproduced by others. This original seedling has since been destroyed.

Of my reproductions of said seedling by budding, only two were preserved, these being registered with the Ohio Agricultural Experiment Station at Wooster, Ohio, for test purposes, in April of 1927. The two trees were planted in the test orchard of that station at Wooster, Ohio, where they are at the present time, being located in accordance with the following description in accordance with the records of said station:

Trees Nos. 101 and 102 in the southwest corner of peach orchard, variety orchard.

Figure 1:
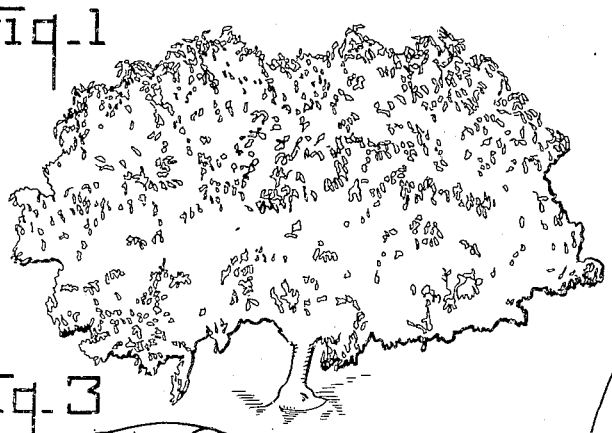
Figure 2:
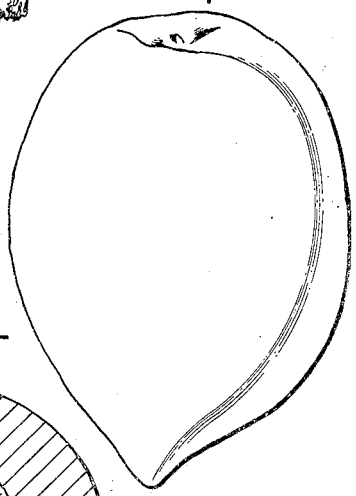
Figure 3:
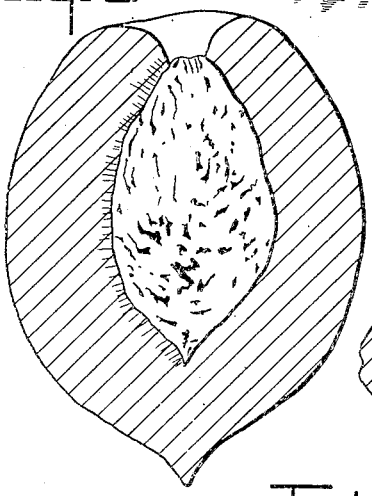
Figure 4:
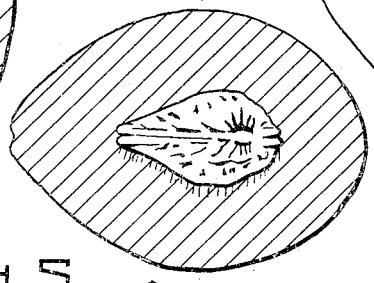
Figure 5:
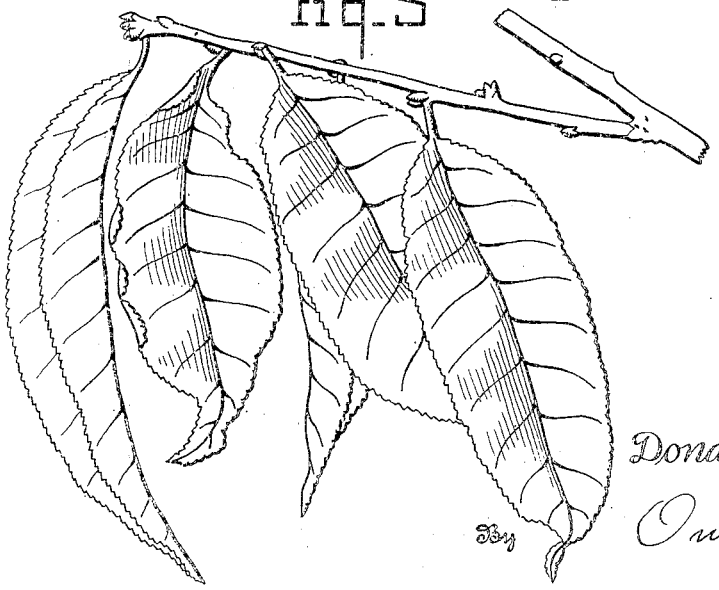

In the accompanying drawing, Figure 1 is an illustration of said Tree No. 101 as it appeared August 8, 1934, and Figure 2 is a perspective of the fruit, while Figs. 3 and 4 are longitudinal and transverse sections, respectively, of the fruit, and Fig. 5 is an enlarged perspective of a twig and leaves.

The new tree illustrated resembles the Elberta peach more than it does any other well-known variety, and, therefore, will be described to a considerable extent in terms of its variation from the Elberta peach tree.

The particular tree illustrated was eleven feet tall and fifteen feet broad in its eighth year, when standing erect. In the accompanying illustration, it is shown loaded with fruit, as it was on August 8th, 1934. It is not as tall or as open growing as Elberta peach trees in the same orchard, but is a vigorous grower and may be classed as intermediate between the Elberta and the J. H. Hale in this respect. The bark on the trunk of the tree is medium as to smoothness.

The leaves are oval to obovate-lanceolate, on the average about six inches long and two inches wide. The upper surface is a dull, dark olive green and the lower surface a grayish green, the entire leaf being somewhat more highly pigmented with yellow than the Elberta. Also the leaves are much curved along the midrib and fold upward along the midrib more than the Elberta. The surface of the leaves is mostly smooth, but slightly rugose near the midrib on the upper surface. The serrations on the leaf's margin vary from fine to coarse, and the margin is generally glandular. In thickness, the leaves vary from medium to thick and leathery. The petiole is about ⅜ inch long, with one to several reniform glands of medium to large size, arranged alternately, and of changing color with the season.

The twigs of the tree are similar to those of the Elberta in shape, color and general characteristics.

The flowering time of the tree at Wooster, Ohio, has ranged for the last five years between April 18th for the first bloom, and May 7th for the last bloom, it being in full bloom usually during the last week of April, but this year, 1934, the first bloom was May 2nd and the last May 7th. This new variety has a larger and more showy bloom than the Elberta, closely resembling the Carman in this respect. The flower buds are pubescent, medium to large in size, medium to long, conic to obtuse, plump, and mostly appressed.

The fruit is a yellow free-stone peach, having a thick skin, and in size, color, texture and juiciness of flesh, flavor and general appearance resembling the Elberta, except that it has a more prominent tip, and that it is more elongated than the Elberta or other known varieties of yellow peaches ripening at about the same time. It is distinguishable from the Elberta by being less plump. The suture is pronounced, there is a tendency to bulge more on one side than on the other, and the apex is decidedly pointed.

The fruit's shipping and keeping qualities are good. It is a good all purpose peach. It is of good quality for dessert, and also cooks and cans well. It is good for home use, and it is also a good market peach.

The ripening time at Wooster, Ohio, is about September 10th, ripening with and a little later than the Elberta.

The particular feature of the original tree which I considered most important was its steady bearing, sure cropping characteristic, and this, with the other characteristics above described, has been reproduced in the reproductions by budding now growing at the said station. The resistance of the tree, leaves and fruit, respectively, to insects and diseases is good. It has resisted well the dry seasons encountered, and is particularly resistant to cold.

That it is more resistant to cold than the Elberta was evident with the original tree and with the said reproductions in past years; but the high degree of its resistance in this respect became fully apparent only this year, when the unusual cold to which it was subjected last winter demonstrated its resistance in this respect and made it apparent that its previously indicated qualities in this respect were so dependable as to render it helpful to make this new variety available to the public.

This last winter it withstood a temperature of —18° F. and produced its usual full crop, so that it had to be thinned. The cold resulted in no crop on Elberta trees in the same test orchard, and a light crop only on Carman trees in the same orchard. No other yellow free-stone peach ripening at about the same time, produced a full, or near full, crop this year in said orchard.

Accordingly the hardiness of this variety in its resistance to cold is an outstanding characteristic.

Having clearly described the new and improved peach tree, what I claim is:

The peach tree of the Elberta type herein described, characterized by the shape of its leaves, its elongated fruit and its resistance to cold.

DONALD S. BYERS.